US00PP09707P

United States Patent [19]

Ohrazda et al.

[11] Patent Number: Plant 9,707

[45] Date of Patent: Nov. 26, 1996

[54] 'LUCKY ROSE GOLDEN' APPLE TREE

[75] Inventors: Melvin Ohrazda, Orondo; David Mathison, Wenatchee, both of Wash.

[73] Assignee: Lucky Stemilt, Wenatchee, Wash.

[21] Appl. No.: 457,287

[22] Filed: May 12, 1995

[51] Int. Cl.[6] ..... A01H 5/00

[52] U.S. Cl. ..... Plt./34.1

[58] Field of Search ..... Plt./34.1, 35, 35.1, Plt./35.2

*Primary Examiner*—James R. Feyrer

*Attorney, Agent, or Firm*—Lane, Aitken & McCann

[57] ABSTRACT

A new variety of apple tree which bears apples with a deep red blush on areas exposed to sunlight is disclosed. The new variety exhibit a blush on a greater percentage of its apples than the Golden Delicious variety. Typically the blush is darker red than the blush exhibited by the fruit of the Golden Delicious variety.

6 Drawing Sheets

BACKGROUND OF THE DISCOVERY

The discovery which is the subject of this patent involves a new and distinct apple tree originating as a whole tree sport or mutation in the Lucky Badger Orchard, Bray's Road, 5 miles north of Orondo, Douglas County, Wash. The new tree variety has been denominated as the "Lucky Rose Golden". The new apple tree was discovered in a cultivated area and more specifically, in an orchard at the above identified location containing trees of the Golden Delicious variety. The orchard in which the new variety was discovered was planted in 1964.

Although the newly discovered tree resembles a Golden Delicious tree, its characteristics clearly distinguish from all previously known varieties of Golden Delicious trees. The new tree variety is best distinguished by its fruit which exhibits a rose-red blush on exposed fruit. The blush is significantly and dramatically deeper red than the blush on apples of Golden Delicious trees which exhibit a blush. An average of 47 percent of fruits exhibit the blushed surface on the Lucky Rose Golden variety, compared to less than 5 percent on conventional Golden Delicious trees. In addition to the distinctive blush, the skin of the fruit of the Lucky Rose golden is lighter in color than fruit from Golden Delicious trees which grow in the same orchard where the new tree was discovered. Another characteristic which distinguishes the new variety is that stems of the apples from the new variety are distinctively shorter than stems of related apple trees. Furthermore, the leaves of the new tree variety are darker green than leaves of golden Delicious apple trees.

The new apple tree variety has been asexually reproduced through successive generations by budding and grafting at the Lucky Badger Orchard. The characteristics manifested in the parent tree appear stable in the propagated plants.

BRIEF DESCRIPTION OF THE DRAWINGS

FIG. 3(*b*) is a bar graph comparing the green chroma values of the skin color of the Lucky Rose apple to the Golden Delicious apple.

FIG. 3(*c*) is a bar graph comparing the yellow chroma values of the skin color of the Lucky Rose apple to the Golden Delicious apple.

FIG. 6(*b*) is a bar graph comparing relative starch content characteristics of the Lucky Rose apple to the Golden Delicious apple.

FIG. 6(*c*) is a bar graph comparing relative soluble solids characteristics of the Lucky Rose apple to the Golden Delicious apple.

FIG. 6(*d*) is a bar graph comparing seed color characteristics of the Lucky Rose apple to the Golden Delicious apple.

DETAILED DESCRIPTION

The applicant believes that the nearest related variety of apple tree to the discovery is the Golden Delicious variety which exhibits a light blush on the apples exposed to sunlight. The new tree was found in an orchard which was cultivated with Golden Delicious trees in 1964. Accordingly, the description of the new tree variety is compared and contrasted with the Golden Delicious variety.

Figure 1:
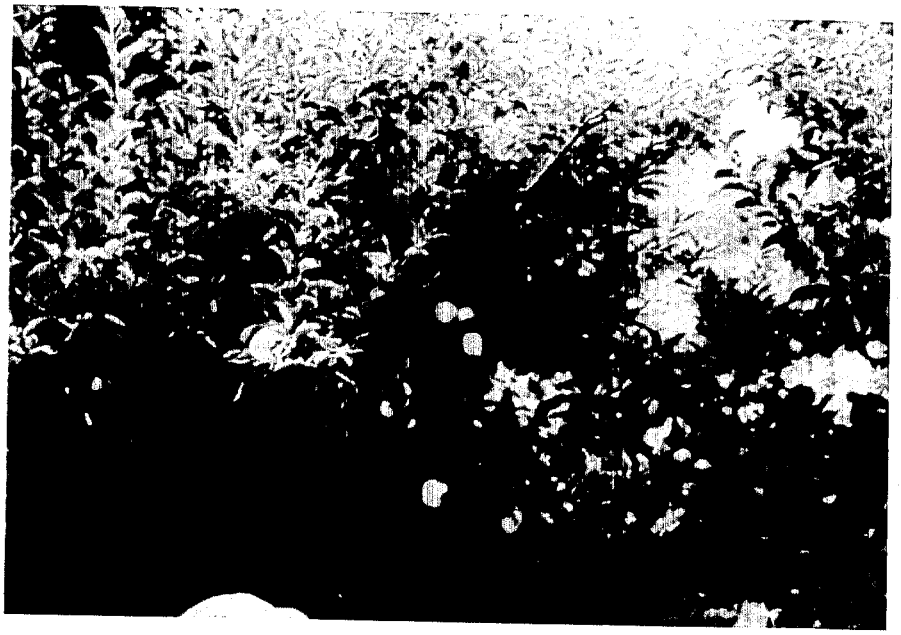
FIG. 1 is a color photograph of the new variety of tree adjacent to a Golden Delicious tree.
Figure 2:
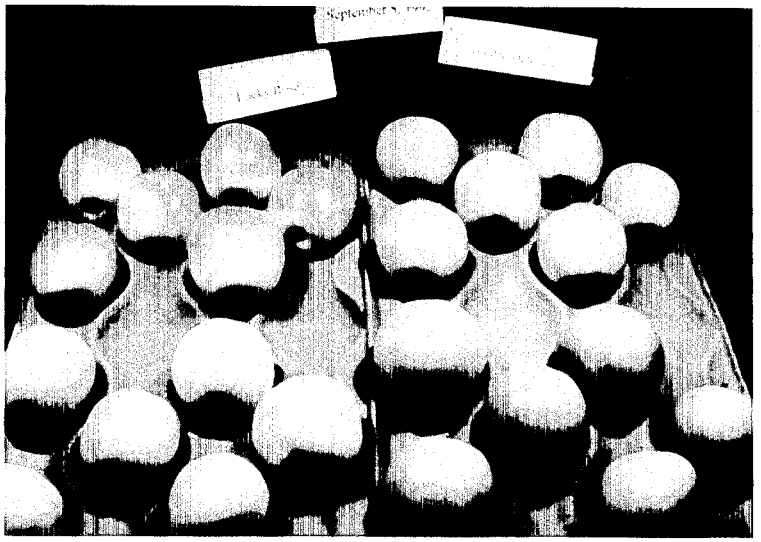
FIG. 2. is a color photograph showing a group of apples of the new variety next to a group of Golden Delicious apples.

The most distinctive characeristic of the new tree variety is the deep red blush on apples which are exposed to sunlight as best seen in FIG. 1. As the photograph demonstrates, the new tree variety can easily be distinguished from the Golden Delicious variety (which is shown on the far right of the photograph) by reference to the red blush on those apples which are exposed to sunlight. FIG. 2, which depicts apples of the Lucky Rose Golden next to apples from a Golden Delicious, also highlights the respective differences in the apples of the two varieties. The new variety, depicted on the left and identified in FIG. 2 as "Lucky Rose", exhibits a siginificantly deeper blush than Golden Delicious apples. The red pigmented blush area is more intense and distributed over a larger surface area than the blush area of the Golden Delicious variety. As best seen in the bottom of the photograph, one can discern that the skin of the apples of the new variety is lighter in color than the skin of the Golden Delicious variety.

Figure 3A:
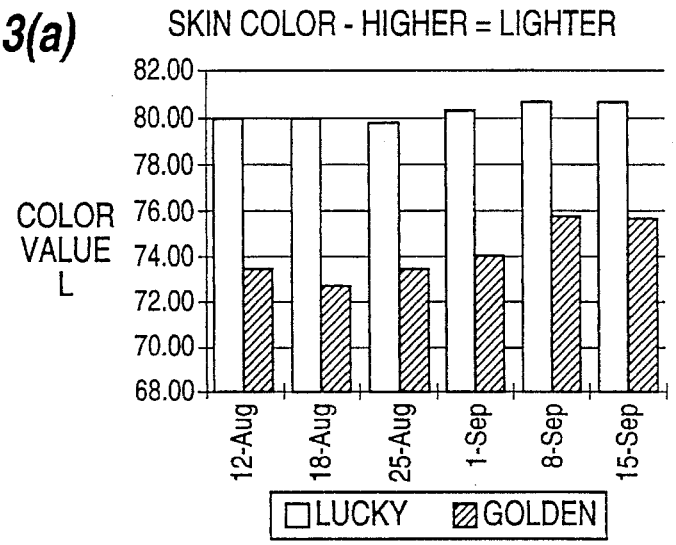
FIG. 3(*a*) is a bar graph comparing the brightness of the skin color of the Lucky Rose apple to the Golden Delicious apple.
Figure 3B:
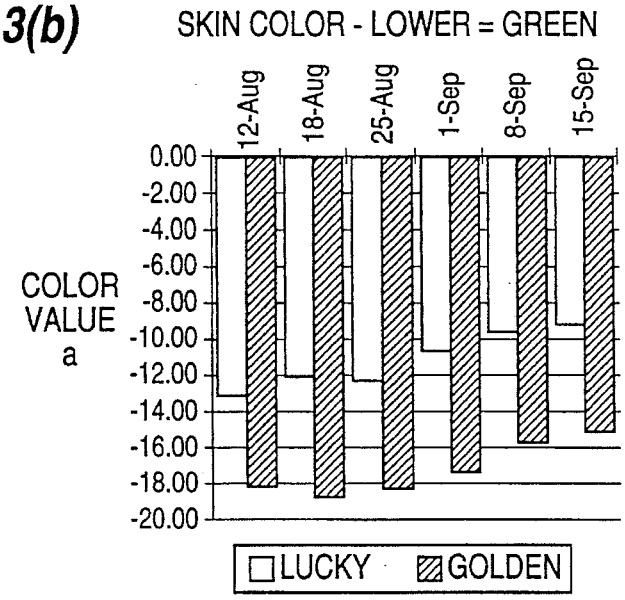
Figure 3C:
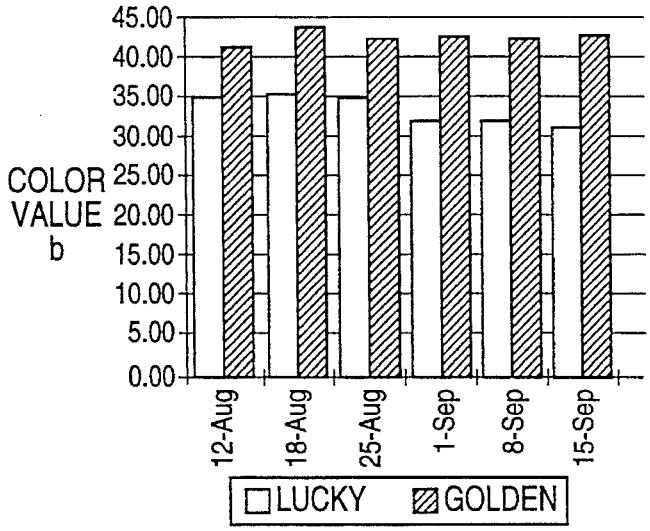

FIGS. 3(*a*)–3(*c*) are bar graphs which chart quantitative data directed at the respective color differences of fruit from the new tree variety and the Golden Delicious variety. The data, generated with a Minolta Chroma meter CR-200, confirms that the skin of the Lucky Rose Golden variety remains significantly ligher than the skin of Golden Delicious apple. The graphs tracks samples picked from Aug. 12, 1994 through Sep. 15, 1994. The graphs indicate that the skin of apples from Lucky Rose Golden trees have consistently lower green and yellow chroma values.

Figure 4:
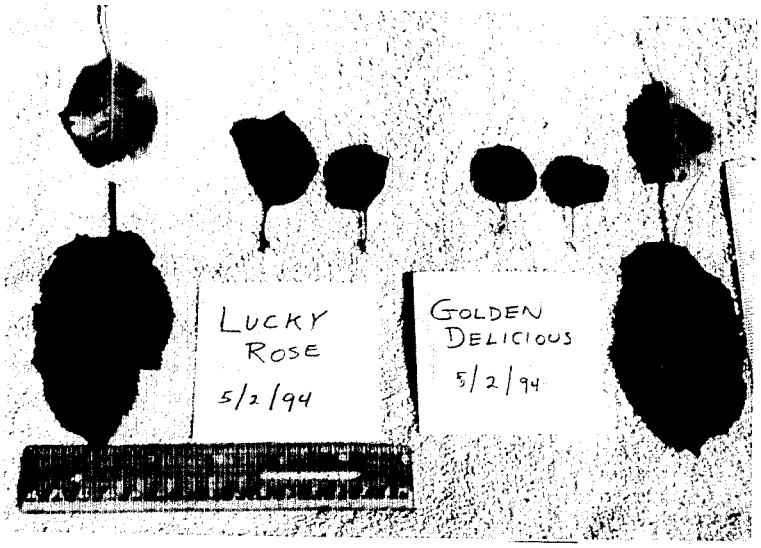
FIG. 4 is a color photograph showing leaves of the Lucky Rose Golden apple tree variety next to leaves of the Golden Delicious variety.

FIG. 4 shows leaves of the new variety next to leaves from a Golden Delicious tree. As the photograph demonstrates, leaves from the Lucky Rose Golden variety are preceptably darker than leaves form Golden Delicious trees. Further analysis comparing the leaves of the Lucky Rose golden and the Golden Delicious was performed and the data that was generated is set forth in Table 1.

TABLE 1

| | Golden Delicious | Lucky Rose Golden | % Delicious from Golden |
|---|---|---|---|
| Leaf weight (g)* | 0.92 | 0.65 | −29.3 |
| Leaf area (sq. cm)* | 35.2 | 25.3 | −28.1 |
| Petiole length (mm)* | 26.3 | 23.9 | −8.8 |
| Petiole diameter (mm)* | 1.37 | 1.22 | −10.9 |
| Leaf color — upper** | −0.79 | −0.87 | 10.1 |
| Leaf color — lower** | −0.61 | −0.60 | −1.6 |

*Average of 50 leaves at each sampling date.
**Minolta Chroma Meter Cr-200 ratio of a/b value. Higher ratio means darker leaf color.

Table 1 reflects a summary of data where approximately fifty leaves were collected, measured and weighed on a number of sampling dates and provides additional quantitative data which distinguish the new variety from the Golden Delicious trees. The data relating to leaf color, is consistent with a qualitative assessment that the leaves of the new tree are darker than leaves from Golden Delicious Trees. The leaves of the new variety are generally smaller than the leaves of the Golden Delicious variety and on average weigh less. Table 1 also sets forth data relating to the color of the lower surface of the leaf and petiole length.

Figure 5:
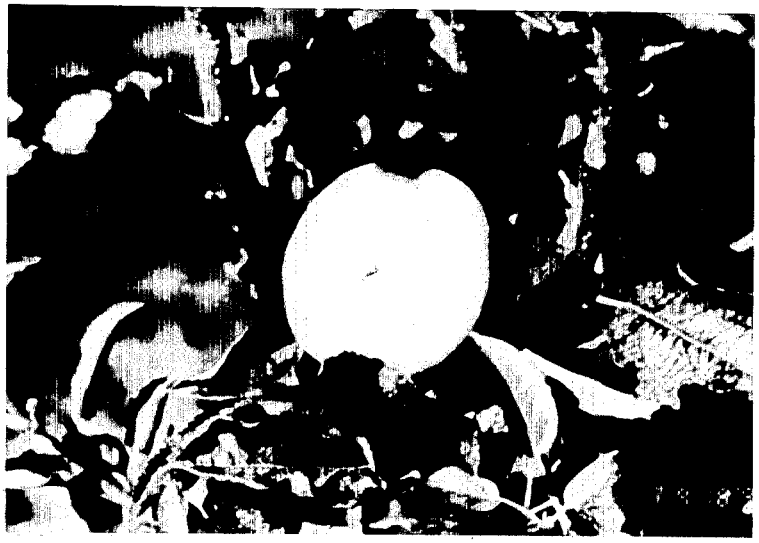
FIG. 5 is a color photograph which shows the stem of the Lucky Rose Golden variety.
Figure 6A:
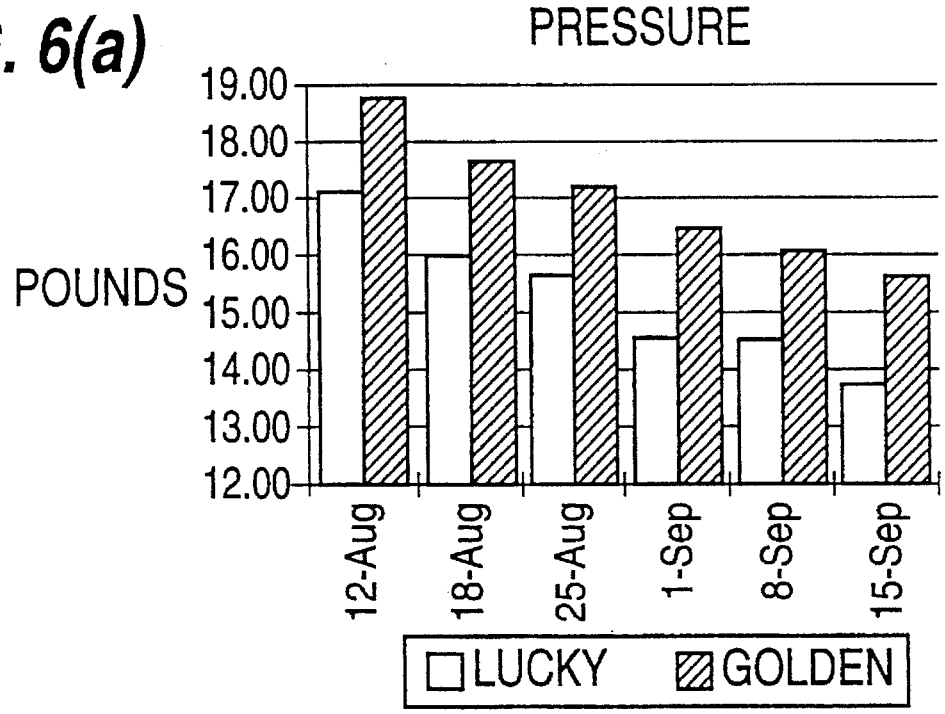
FIG. 6(*a*) is a bar graph comparing relative pressure characteristics of the Lucky Rose apple to the Golden Delicious apple.
Figure 6B:
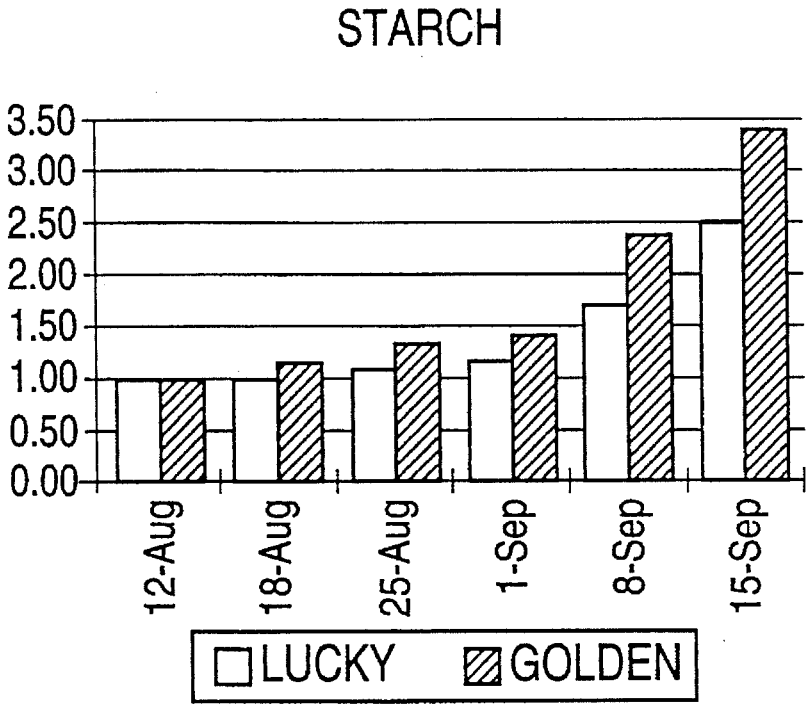
Figure 6C:
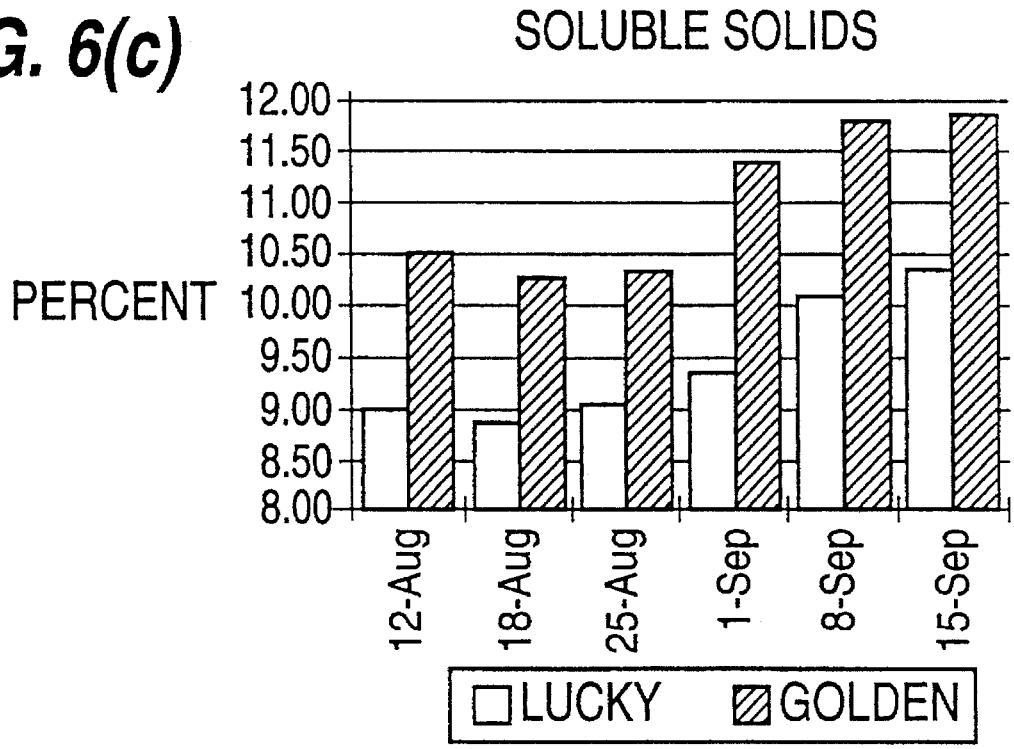
Figure 6D:
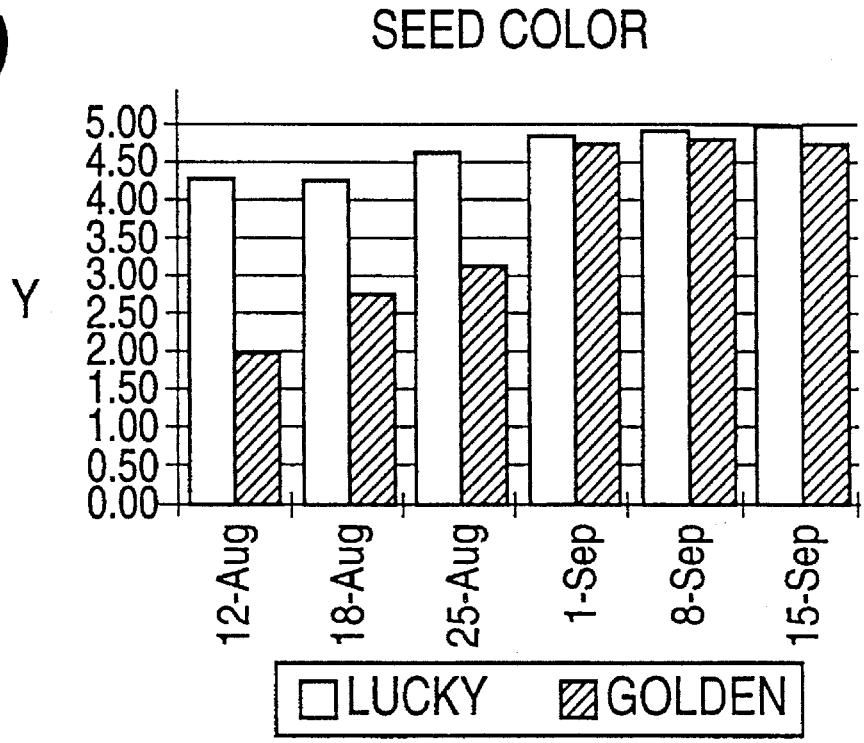

As can be seen in FIG. 5, a photograph of the stem of the new variety, a further distinction between the new variety and the Golden Delicious variety is the relative size of the stems of the fruit. On average, the stems of penduncles of the new variety are approximately 33% shorter than stems of the Golden Delicious variety. The stems of the new variety are also thicker than stems of the Golden Delicious variety and, as a result, the fruit attached by the stem are slightly more difficult to pick than other apples.

Figure 7:
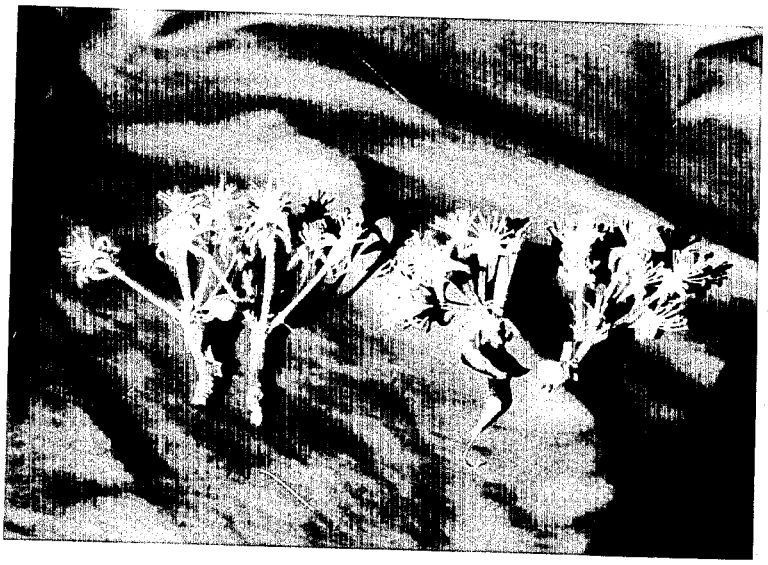
FIG. 7 is a color photograph of flowers of both the Lucky Rose Golden and the Golden Delicious at the petal-full stage of development.

FIG. 7 also highlights the difference in respective sizes of the peduncles of the Lucky Rose Golden and the golden Delicious trees. The Lucky Rose Golden variety, depicted on the right, have conspicuously shorter penduncles than those on the Golden Delicious variety which is set forth on the left.

In addition to the visual differences, the fruit of the new variety differs from the Golden Delicious in both composition and consistency. Referring to FIG. 6(*a*), the pressure or firmness of the new variety is significantly less than the pressure of the Golden Delicious when measured over a three month period. The pressure data set forth in FIG. 6(*b*) was generated with a Magnass-Taylor pressure tester. Depicted in FIG. 6(*c*) is a comparison of the relative soluable solids of Lucky Rose Gold Delicious apples and conventional Golden Delicious apples. The relative soluble solids of the new variety compared over a period from Aug. 15, 1994 until Sep. 15, 1994 were consistently less than Golden Delicious apples. The data set forth in FIG. 6(*b*) also reflects that as the apples ripen, the production of starch by the new variety is less than the starch content of apples produced by the Golden Delicious variety.

The following botanical description further identifies the unique characteristics of the new variety.

BOTANICAL DESCRIPTION

Parentage: Single bud mutation for Golden Delicious, leading to whole tree mutation.

Location of parent tree: Lucky Badger Orchard, Bray's Road, 5 miles north of Orondo, Douglas County, Wash., USA.

Date of discovery: October 1987.

Date of fruit maturity: Approximately 7 days before Golden Delicious, using pressure as primary indicator of maturity. May require 2 picks.

Tree: Medium vigor, upright spreading, hardy, productive, annual bearer.

Trunk: Stocky, smooth, gray-green to light brown.

Branches: Spreading, wide angles, medium thick, lenticels cream colored, elongated.

Internodes: Average internode length 22 mm (same as in Golden Delicious—21.6 mm).

Leaves (primary): Broad, dark green, medium glossy on upper surface, finely pubescent on lower surface (indistinguishable from those of Golden Delicious).

*Length.*—70–105 mm.

*Width.*—45–50 mm.

*Petiole.*—Medium to long (30–35 mm); thin (1.5–1.7 mm); finely pubescent.

*Margins.*—Serrate.

*Tip.*—Sharply pointed.

*Stipules* (*bracts*).—Insignificant, borne in pairs opposite, narrow, pointed, 5 mm in length, borne 2 mm from abscission zone.

*Color.*—#21-14 (upper), #21-11 (lower) (Munsell Limited Color Cascade).

Leaves (secondary): Oval, dark green upper surface, finely pubescent lower surface.

*Length.*—40–60 mm.

*Width.*—30–40 mm.

*Margins.*—Finely serrate.

*Tip.*—Pointed.

*Stipules* (*bracts*).—Identical to primary leaves.

Flowers: Mid-season (full bloom April 18–22 at Orondo, Wash.).

*Size.*—Medium.

*Color.*—White.

*Stamen.*—Single row, anthers bright yellow, turining yellowish brown with pollen shed.

*Pistil.*—Stigmas medium, flat at top, rounded at base; styles medium long, fused at base.

Sepals.—Medium size, pubescent.

Pollination requirements.—Satisfied by other diploid strains, such as Red Delicious (but not Golden Delicious), Winter Banana, Granny Smith, and commonly used strains of crabapples. No fruit produced from self-pollination. Pollination trials showed Lucky Rose Golden to be an excellent pollinizer for Jonagold, Fuji and Gala.

Fruit:

Maturity when described.—Ripe (starch content 4.0–5.0).

Size.—Medium (75 mm) to large (90 mm). Average weight 250 grams.

Form.—Conical with moderate lobes at calyx end.

Cavity.—Round, medium deep; apex acute; breadth 35 mm, depth 18 mm.

Basin (calyx),—Very small, acuminate, slightly furrowed; calyx tightly closed, lobes small and converged from base toward center, finely publescent.

Stem.—Short and moderatly thick—24.6 mm×2.0 mm, compared to Golden Delicious—36.6 mm×1.7 mm (FIG. 3).

Skin.—Unusually glossy, smooth, without bloom, #29-2 (Munsell Limited Color Cascade) ground color yellow; overcolor bright pink blush #38-9, most prominent toward shoulder on exposed fruits (FIG. 9); lenticels incomspicuous, small, widely scattered, no tendency to russet as with Golden Delicious. Greasiness of skin absent; cracking tendency absent; skin thickness medium.

Flesh.—Cream becoming pale glow with advanced maturity, crisp, juicy, tender. Flavor is good, refreshing, but less sweet than that of Golden Delicious (FIG. 1). No water core.

Aroma.—Mild, with a citrus-like fragrance.

Core.—(longitudinal section) Broadly ovate, symmetrical; (cross section) round, medium size, seed cells open.

Seeds.—Normally 10–12, 2.1 per cell, medium brown; length 7 mm, width 4 mm.

Use: Fresh, dessert.

Storage: Up to 9 months in CA, 4–5 months in regular storage at 32 degrees F. (0 degrees C.).

We claim:

1. The new and distinct variety of apple tree as illustrated and described, characterized by the light skin, an intense blush on exposed areas, a short stem, and a darker leaf than the Golden Delicious.

* * * * *